(12) United States Patent
Maurer et al.

(10) Patent No.: US 9,561,995 B2
(45) Date of Patent: Feb. 7, 2017

(54) PROCESS FOR THE RECOVERY OF COMPONENTS FORMING A METAL-ORGANIC FRAMEWORK MATERIAL

(71) Applicant: BASF SE, Ludwigshafen (DE)

(72) Inventors: Stefan Maurer, Ludwigshafen (DE); Hendrick Mattenheimer, Ludwigshafen (DE); Ulrich Müller, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/022,960

(22) PCT Filed: Sep. 22, 2014

(86) PCT No.: PCT/IB2014/064724
§ 371 (c)(1),
(2) Date: Mar. 18, 2016

(87) PCT Pub. No.: WO2015/040593
PCT Pub. Date: Mar. 26, 2015

(65) Prior Publication Data
US 2016/0221920 A1    Aug. 4, 2016

(30) Foreign Application Priority Data
Sep. 23, 2013 (EP) ..................... 13185532

(51) Int. Cl.
| C07C 51/00 | (2006.01) |
| C07C 51/487 | (2006.01) |
| B01D 11/02 | (2006.01) |
| B01J 20/22 | (2006.01) |
| B01J 20/30 | (2006.01) |

(52) U.S. Cl.
CPC ............ C07C 51/487 (2013.01); B01D 11/02 (2013.01); B01J 20/226 (2013.01); B01J 20/3085 (2013.01)

(58) Field of Classification Search
CPC .............................. C07C 51/487; B01J 20/226
USPC ......................................................... 562/487
See application file for complete search history.

(56) References Cited

U.S. PATENT DOCUMENTS

| 5,648,508 A | 7/1997 | Yaghi |
| 7,119,219 B2 | 10/2006 | Mueller et al. |
| 7,534,303 B2 | 5/2009 | Mueller et al. |
| 7,815,716 B2 | 10/2010 | Mueller et al. |
| 8,163,949 B2 | 4/2012 | Mueller et al. |
| 8,372,998 B2 | 2/2013 | Schubert et al. |
| 2005/0004404 A1 | 1/2005 | Muller et al. |
| 2010/0166644 A1 | 7/2010 | Schubert et al. |
| 2012/0141685 A1 | 6/2012 | Gaab et al. |

FOREIGN PATENT DOCUMENTS

| DE | 101 11 230 A1 | 9/2002 |
| DE | 103 55 087 A1 | 6/2005 |
| DE | 10 2005 053430 A1 | 5/2007 |
| EP | 0 102 544 A2 | 3/1984 |
| EP | 0200260 A2 | 12/1986 |
| EP | 0389041 A1 | 9/1990 |
| EP | 0592050 A1 | 4/1994 |
| EP | 0 790 253 A2 | 8/1997 |
| EP | 1 702 925 A1 | 9/2006 |
| EP | 2230288 A2 | 9/2010 |
| JP | H0337156 A | 2/1991 |
| WO | WO-94/13584 A1 | 6/1994 |
| WO | WO-94/29408 A1 | 12/1994 |
| WO | WO-95/19222 A1 | 7/1995 |
| WO | WO-2005/003622 A1 | 1/2005 |
| WO | WO-2005/049892 A1 | 6/2005 |
| WO | WO-2007/023134 A1 | 3/2007 |
| WO | WO-2007/054581 A2 | 5/2007 |
| WO | WO-2007/090809 A1 | 8/2007 |
| WO | WO-2012/042410 A1 | 4/2012 |

OTHER PUBLICATIONS

International Search Report for PCT/IB2014/064724 mailed Jan. 26, 2015.
Millward, A., et al., "Metal-Organic Frameworks with Exceptionally High Capacity for Storage of Carbon Dioxide at Room Temperature", Journal of the American Chemical Society, vol. 127, No. 51, (2005), pp. 17998-17999.

*Primary Examiner* — Sikarl Witherspoon
(74) *Attorney, Agent, or Firm* — Drinker Biddle & Reath LLP

(57) ABSTRACT

The present invention relates to a process for the recovery of an at least bidentate organic compound comprised in a porous metal-organic framework material, the material comprising the at least bidentate organic compound coordinated to at least one metal ion, the process comprising the steps of (a) treating the metal-organic framework material with an acidic or alkaline liquid; (b) optionally separating off solid residue; and (c) isolating the at least bidentate organic compound.

18 Claims, No Drawings

PROCESS FOR THE RECOVERY OF COMPONENTS FORMING A METAL-ORGANIC FRAMEWORK MATERIAL

CROSS-REFERENCE TO RELATED APPLICATIONS

This application is a national stage application (under 35 U.S.C. §371) of PCT/IB2014/064724, filed Sep. 22, 2014, which claims benefit of European Application No. 13185532.2, filed Sep. 23, 2013, both applications of which are incorporated herein by reference in their entirety.

The present invention relates a process for the recovery of an at least bidentate organic compound comprised in a porous metal-organic framework material, the material comprising the at least bidentate organic compound coordinated to at least one metal ion.

DETAILED DESCRIPTION OF THE INVENTION

The usage of metal-organic framework material as adsorbents for example in natural gas storage tanks for automotive requires a careful look into the whole lifecycle of the application. With respect to automotive applications after exceeding the lifetime of the vehicle the tanks containing the metal-organic framework material will be dismantled and the adsorbent has to either be disposed or treated somehow else. Most beneficial from both ecological and economical view would be a simple recycling procedure allowing to re-obtain at least the organic linker in high yields and the reuse in the corresponding synthesis of fresh metal-organic framework material.

Thus, an object of the present invention is to find a simple solution for recycling of components (or at least the organic ligand) forming a metal-organic framework material on a solid ecological and economical foundation.

The object is achieved by a process for the recovery of an at least bidentate organic compound comprised in a porous metal-organic framework material, the material comprising the at least bidentate organic compound coordinated to at least one metal ion, the process comprising the steps of
  (a) treating the metal-organic framework material with an acidic or alkaline liquid;
  (b) optionally separating off solid residue;
  (c) isolating the at least bidentate organic compound.

It was surprisingly found that the at least bidentate organic compound (ligand) can be recovered in high yields and good purities so that the recovered ligand can be re-used for example for the preparation of new metal-organic framework materials. Furthermore also the metal ion can be recovered and re-used.

According to the present invention an at least bidentate organic compound (also called "linker"), which participates in the formation of a metal-organic framework material (also called "metal-organic framework" or "MOF") by coordinating at least one metal ion is recovered.

The porous metal-organic framework can be present in powder form or as shaped bodies.

Such metal-organic frameworks (MOFs) are known in the prior art and are described, for example, in U.S. Pat. No. 5,648,508, EP-A-0 790 253, M. O'Keeffe et al., J. Sol. State Chem., 152 (2000), pages 3 to 20, H. Li et al., Nature 402, (1999), page 276, M. Eddaoudi et al., Topics in Catalysis 9, (1999), pages 105 to 111, B. Chen at al., Science 291, (2001), pages 1021 to 1023, DE-A-101 11 230, DE-A 10 2005 053430, WO-A 2007/054581, WO-A 2005/049892 and WO-A 2007/023134.

The general suitability of metal-organic frameworks for the sorption of gases and liquids is described, for example, in WO-A 2005/003622 and EP-A 1 702 925.

The metal-organic frameworks of the present invention comprise pores, in particular micropores and/or mesopores. Micropores are defined as pores having a diameter of 2 nm or less and mesopores are defined by a diameter in the range from 2 to 50 nm, in each case in accordance with the definition given in Pure & Applied Chem. 57 (1983), 603-619, in particular on page 606. The presence of micropores and/or mesopores can be checked by means of sorption measurements which determine the uptake capacity of the MOF for nitrogen at 77 Kelvin in accordance with DIN 66131 and/or DIN 66134.

The specific surface area, calculated according to the Langmuir model (DIN 66131, 66134), of a MOF in powder form is preferably greater than 1 $m^2/g$, more preferably greater than 10 $m^2/g$, more preferably greater than 100 $m^2/g$, more preferably above 300 $m^2/g$, more preferably greater than 700 $m^2/g$, even more preferably greater than 800 $m^2/g$.

Shaped bodies comprising metal-organic frameworks can have a lower active surface area, but this is preferably greater than 1 $m^2/g$, more preferably greater than 10 $m^2/g$, even more preferably greater than 100 $m^2/g$.

However, the metal-organic framework material in the process of the present invention is already used in any application so that the pores can be already occupied by sorbed material, like gases, liquids or the like. Thus, according to the present invention the term "porous" means a porous material, where the porosity is or was given. Thus the porosity can be measured directly or after removal of such sorbed material (or at least partly removed), e.g. by heat treatment.

As a consequence the metal-organic framework material can be unused or used material, preferably used material is employed.

The metal component in the framework according to the present invention is preferably selected from groups Ia, IIa, IIIa, IVa to VIIIa and Ib to VIb. Particular preference is given to Li, Na, Mg, Ca, Sr, Ba, Sc, Y, Ln, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, Al, Ga, In, Tl, Si, Ge, Sn, Pb, As, Sb and Bi, where Ln represents lanthanides.

Lanthanides are La, Ce, Pr, Nd, Pm, Sm, En, Gd, Tb, Dy, Ho, Er, Tm, Yb.

With regard to the ions of these elements, particular mention may be made of $Li^+$, $Na^+$, $Mg^{2+}$, $Ca^{2+}$, $Sr^{2+}$, $Ba^{2+}$, $Sc^{3+}$, $Y^{3+}$, $Ln^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{1+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$.

Particular preference is given to Mg, Al, Li, Ca, Zr, Ti, V, Cr, Mo, Fe, Co, Cu, Ni, Zn, La. Greater preference is given to Al, Mo, Mg, Fe, Cu and Zn. Very particular preference is given to Al, Cu, Mg and Zn, especially Al, Cu and Zn.

The term "at least bidentate organic compound" refers to an organic compound which comprises at least one functional group which is able to form at least two coordinate bonds to a given metal ion and/or a coordinate bond to each of two or more, preferably two, metal atoms.

As functional groups via which the coordinate bonds mentioned can be formed, particular mention may be made of, for example, the following functional groups: —$CO_2H$, —$CS_2H$, —$NO_2$, —$B(OH)_2$, —$SO_3H$, —$Si(OH)_3$, —$Ge(OH)_3$, —$Sn(OH)_3$, —$Si(SH)_4$, —$Ge(SH)_4$, —$Sn(SH)_3$, —$PO_3H$, —$AsO_3H$, —$AsO_4H$, —$P(SH)_3$, —$As(SH)_3$, —$CH(RSH)_2$, —$C(RSH)_3$, —$CH(RNH_2)_2$, —$C(RNH_2)_3$, —$CH(ROH)_2$, —$C(ROH)_3$, —$CH(RCN)_2$, —$C(RCN)_3$, where R is, for example, preferably an alkylene group having 1, 2, 3, 4 or 5 carbon atoms, for example a methylene, ethylene, n-propylene, i-propylene, n-butylene, i-butylene, tert-butylene or n-pentylene group, or an aryl group comprising 1 or 2 aromatic rings, for example 2 $C_6$ rings, which may, if appropriate, be fused and may be independently substituted by at least one substituent in each case and/or may comprise, independently of one another, at least one heteroatom such as N, O and/or S. In likewise preferred embodiments, functional groups in which the abovementioned radical R is not present are possible. Such groups are, inter alia, —$CH(SH)_2$, —$C(SH)_3$, —$CH(NH_2)_2$, —$C(NH_2)_3$, —$CH(OH)_2$, —$C(OH)_3$, —$CH(CN)_2$ or —$C(CN)_3$.

The at least two functional groups can in principle be any suitable organic compound, as long as it is ensured that the organic compound in which these functional groups are present is capable of forming the coordinate bond and producing the framework.

The organic compounds which comprise the at least two functional groups are preferably derived from a saturated or unsaturated aliphatic compound or an aromatic compound or a both aliphatic and aromatic compound.

The term "derived from" means that the organic compound is present in the metal-organic framework material in fully or partly deprotonated form or without any deprotonation. For example a carboxylic acid used as at least bidentate organic compound can be present in the metal-organic framework at least partly as carboxylate. However, also the carboxylic acid may be present. The term "derived from" also encompasses substituted derivatives of the organic compounds; however, this is not preferred. Suitable substituents are hydroxyl, methyl, ethyl, fluoro, chloro, bromo, amino ($NH_2$), phenyl, benzyl.

The aliphatic compound or the aliphatic part of the both aliphatic and aromatic compound can be linear and/or branched and/or cyclic, with a plurality of rings per compound also being possible. More preferably, the aliphatic compound or the aliphatic part of the both aliphatic and aromatic compound comprises from 1 to 15, more preferably from 1 to 14, more preferably from 1 to 13, more preferably from 1 to 12, more preferably from 1 to 11 and particularly preferably from 1 to 10, carbon atoms, for example 1, 2, 3, 4, 5, 6, 7, 8, 9 or 10 carbon atoms. Particular preference is here given to, Inter alia, methane, adamantane, acetylene, ethylene or butadiene.

The aromatic compound or the aromatic part of the both aromatic and aliphatic compound can have one or more rings, for example two, three, four or five rings, with the rings being able to be separate from one another and/or at least two rings being able to be present in fused form. The aromatic compound or the aromatic part of the both aliphatic and aromatic compound particularly preferably has one, two or three rings, with one or two rings being particularly preferred. Furthermore, each ring of the specified compound can independently comprise at least one heteroatom such as N, O, S, B, P, Si, Al, preferably N, O and/or S. The aromatic compound or the aromatic part of the both aromatic and aliphatic compound more preferably comprises one or two $C_6$ rings which are present either separately or in fused form.

Particular mention may be made of benzene, naphthalene and/or biphenyl and/or bipyridyl and/or pyridyl as aromatic compounds.

The at least bidentate organic compound is more preferably an aliphatic or aromatic, acyclic or cyclic hydrocarbon which has from 1 to 18, preferably from 1 to 10 and in particular 6, carbon atoms and also has exclusively 2, 3 or 4 carboxyl groups as functional groups.

Preferably, the at least bidentate organic compound is derived from a di- tri- or tertracarbocyclic acid.

For example, the at least bidentate organic compound is derived from a dicarboxylic acid such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidecarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyrane-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octadicarboxylic acid, pentane-3,3-carboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran 250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindandicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenon-dicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diamino(diphenyl ether)diimidedicarboxylic acid, 4,4'-diaminodiphenylmethanediimidedicarboxylic acid, 4,4'-diamino(diphenyl sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenecarboxylic acid, 8-sulfo-2,3-naphthalenedicarboxylic acid, anthracene-2,3-dicarboxylic acid, 2',3'-diphenyl-p-terphenyl-4,4''-dicarboxylic acid, (diphenyl ether)-4,4'-dicarboxylic acid, imidazole-4,5-dicarboxylic acid, 4(1H)-oxothiochromene-2,8- dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptadicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenon-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbornane-2,3-dicarboxylic acid, 5-ethyl-2,3-pyridinedicarboxylic acid or camphordicarboxylic acid.

Furthermore, the at least bidentate organic compound is more preferably one of the dicarboxylic acids mentioned by way of example above as such (with further substitution).

For example, the at least bidentate organic compound can be derived from a tricarboxylic acid such as 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

Furthermore, the at least bidentate organic compound is more preferably one of the tricarboxylic acids mentioned by way of example above as such (without further substitution).

Examples of an at least bidentate organic compound derived from a tetracarboxylic acid are 1,1-dioxidoperylo[1,12-BCD]thiophene-3,4,9,10-tetracarboxylic acid, perylenetetracarboxylic acids such as perylene-3,4,9,10-tetracarboxylic acid or (perylene-1,12-sulfone)-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenontetracarboxylic acid, 3,3',4,4'-benzophenontetracarboxylic acid, tetrahydrofurantetracarboxylic acid or cyclopentanetetracarboxylic acids such as cyclopentane-1,2,3,4-tetracarboxylic acid.

Furthermore, the at least bidentate organic compound is more preferably one of the tetracarboxylic acids mentioned by way of example above as such (without further substitution).

Very particular preference is given to optionally at least monosubstituted aromatic dicarboxylic, tricarboxylic or tetracarboxylic acids having one, two, three, four or more rings, with each of the rings being able to comprise at least one heteroatom and two or more rings being able to comprise identical or different heteroatoms. For example, preference is given to one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, and preferred heteroatoms are N, S and/or O. Suitable substituents here are, inter alia, —OH, a nitro group, an amino group and an alkyl or alkoxy group.

Particularly preferred at least bidentate organic compounds are imidazolates such as 2-methylimidazolate, acetylenedicarboxylic acid (ADC), camphordicarboxylic acid, fumaric acid, succinic acid, benzenedicarboxylic acids such as phthalic acid, isophthalic acid, terephthalic acid (BDC), aminoterephthalic acid, naphthalenedicarboxylic acids (NDC), biphenyldicarboxylic acids such as 4,4'-biphenyldicarboxylic acid (BPDC), pyrazinedicarboxylic acids such as 2,5-pyrazinedicarboxylic acid, bipyridinedicarboxylic acids such as 2,2-bipyridinedicarboxylic acids such as 2,2'-bipyridine-5,5'-dicarboxylic acid, benzenetricarboxylic acids such as 1,2,3-, 1,2,4-benzenetricarboxylic acid or 1,3,5-benzenetricarboxylic acid (BTC), benzenetetracarboxylic acid, adamantanetetracarboxylic acid (ATC), adamantanedibenzoate (ADB), benzenetribenzoate (BTB), methanetetrabenzoate (MTB), adamantanetetrabenzoate or dihydroxyterephthalic acids such as 2,5-dihydroxyterephthalic acid (DHBDC), tetrahydropyrene-2,7-dicarboxylic acid (HPDC), biphenyltetracarboxylic acid (BPTC).

Very particular preference is given to using, inter alia, phthalic acid, isophthalic acid, terephthalic acid, 2,6-naphthalenedicarboxylic acid, 1,4-naphthalenedicarboxylic acid, 1,5-naphthalenedicarboxylic acid, 1,2,3-benzenetricarboxylic acid, 1,2,4-benzenetricarboxylic acid, 1,3,5-benzenetricarboxylic acid, 1,2,4,5-benzenetetracarboxylic acid, aminoBDC, fumaric acid, biphenyldicarboxylate, 1,5- and 2,6-naphthalenedicarboxylic acid, tert-butylisophthalic acid, dihydroxybenzoic acid, BTB, HPDC, BPTC.

Even more preferred are 1,3,5-tri-(4-carboxyphenyl)-benzene, dihydroxyterephthalic acid, benzene-tricarboxylic acid (especially 1,3,5-BTC) and fumaric acid, especially BTB, BTC and fumaric acid. Even more preferred BTB.

Apart from these at least bidentate organic compounds, the metal-organic framework can also comprise one or more monodentate ligands and/or one or more at least bidentate ligands which are not derived from a dicarboxylic, tricarboxylic or tetracarboxylic acid.

Apart from these at least bidentate organic compounds, the metal-organic framework can also comprise one or more monodentate ligands.

Suitable solvents for preparing the metal-organic framework are, inter alia, ethanol, dimethylformamide, toluene, methanol, chlorobenzene, diethylformamide, dimethyl sulfoxide, water, hydrogen peroxide, methylamine, sodium hydroxide solution, N-methylpyrrolidone ether, acetonitrile, benzyl chloride, triethylamine, ethylene glycol and mixtures thereof. Further metal ions, at least bidentate organic compounds and solvents for the preparation of MOFs are described, inter alia, in U.S. Pat. No. 5,648,508 or DE-A 101 11 230.

The pore size of the metal-organic framework can be controlled by selection of the appropriate ligand and/or the at least bidentate organic compound. In general, the larger the organic compound, the larger the pore size. The pore size is preferably from 0.2 nm to 30 nm, particularly preferably in the range from 0.3 nm to 3 nm, based on the crystalline material.

However, larger pores whose size distribution can vary also occur in a shaped body comprising a metal-organic framework. Preference is nevertheless given to more than 50% of the total pore volume, in particular more than 75%, being made up by pores having a pore diameter of up 1000 nm. However, preference is given to a major part of the pore volume being made up by pores from two diameter ranges. It is therefore more preferred that more than 25% of the total pore volume, in particular more than 50% of the total pore volume, is formed by pores which are in a diameter range from 100 nm to 800 nm and that more than 15% of the total pore volume, in particular more than 25% of the total pore volume, is formed by pores which are in a diameter range up to 10 nm. The pore distribution can be determined by means of mercury porosimetry. However since used material typically has adsorbed agents in the pores a measurement of the pore size may be carried out after removing such agents, e.g. by thermal treatment.

Examples of metal-organic frameworks are given below. In addition to the designation of the framework, the metal and the at least bidentate ligand, the solvent and the cell parameters (angles $\alpha$, $\beta$ and $\gamma$ and the dimensions A, B and C in Å) are indicated. The latter were determined by X-ray diffraction.

| MOF-n | Constituents molar ratio M + L | Solvents | $\alpha$ | $\beta$ | $\gamma$ | a | b | c | Space group |
|---|---|---|---|---|---|---|---|---|---|
| MOF-0 | $Zn(NO_3)_2 \cdot 6H_2O$ $H_3(BTC)$ | ethanol | 90 | 90 | 120 | 16.711 | 16.711 | 14.189 | P6(3)/Mcm |
| MOF-2 | $Zn(NO_3)_2 \cdot 6H_2O$ (0.246 mmol) $H_2(BDC)$ (0.241 mmol) | DMF Toluene | 90 | 102.8 | 90 | 6.718 | 15.49 | 12.43 | P2(1)/n |
| MOF-3 | $Zn(NO_3)_2 \cdot 6H_2O$ (1.89 mmol) $H_2(BDC)$ (1.93 mmol) | DMF MeOH | 99.72 | 111.11 | 108.4 | 9.726 | 9.911 | 10.45 | P-1 |
| MOF-4 | $Zn(NO_3)_2 \cdot 6H_2O$ (1.00 mmol) $H_3(BTC)$ (0.5 mmol) | ethanol | 90 | 90 | 90 | 14.728 | 14.728 | 14.728 | P2(1)3 |
| MOF-5 | $Zn(NO_3)_2 \cdot 6H_2O$ (2.22 mmol) $H_2(BDC)$ (2.17 mmol) | DMF Chlorobenzene | 90 | 90 | 90 | 25.669 | 25.669 | 25.669 | Fm-3m |
| MOF-38 | $Zn(NO_3)_2 \cdot 6H_2O$ (0.27 mmol) $H_3(BTC)$ (0.15 mmol) | DMF Chlorobenzene | 90 | 90 | 90 | 20.657 | 20.657 | 17.84 | I4cm |
| MOF-31 $Zn(ADC)_2$ | $Zn(NO_3)_2 \cdot 6H_2O$ 0.4 mmol $H_2(ADC)$ 0.8 mmol | ethanol | 90 | 90 | 90 | 10.821 | 10.821 | 10.821 | Pn(-3)m |
| MOF-12 $Zn_2(ATC)$ | $Zn(NO_3)_2 \cdot 6H_2O$ 0.3 mmol $H_4(ATC)$ 0.15 mmol | ethanol | 90 | 90 | 90 | 15.745 | 16.907 | 18.167 | Pbca |
| MOF-20 ZnNDC | $Zn(NO_3)_2 \cdot 6H_2O$ 0.37 mmol $H_2NDC$ 0.36 mmol | DMF Chlorobenzene | 90 | 92.13 | 90 | 8.13 | 16.444 | 12.807 | P2(1)/c |
| MOF-37 | $Zn(NO_3)_2 \cdot 6H_2O$ 0.2 mmol $H_2NDC$ 0.2 mmol | DEF Chlorobenzene | 72.38 | 83.16 | 84.33 | 9.952 | 11.576 | 15.556 | P-1 |
| MOF-8 $Tb_2(ADC)$ | $Tb(NO_3)_3 \cdot 5H_2O$ 0.10 mmol $H_2ADC$ 0.20 mmol | DMSO MeOH | 90 | 115.7 | 90 | 19.83 | 9.822 | 19.183 | C2/c |
| MOF-9 $Tb_2(ADC)$ | $Tb(NO_3)_3 \cdot 5H_2O$ 0.08 mmol $H_2ADB$ 0.12 mmol | DMSO | 90 | 102.09 | 90 | 27.056 | 16.795 | 28.139 | C2/c |
| MOF-6 | $Tb(NO_3)_3 \cdot 5H_2O$ 0.30 mmol $H_2(BDC)$ 0.30 mmol | DMF MeOH | 90 | 91.28 | 90 | 17.599 | 19.996 | 10.545 | P21/c |
| MOF-7 | $Tb(NO_3)_3 \cdot 5H_2O$ 0.15 mmol $H_2(BDC)$ 0.15 mmol | $H_2O$ | 102.3 | 91.12 | 101.5 | 6.142 | 10.069 | 10.096 | P-1 |
| MOF-69A | $Zn(NO_3)_2 \cdot 6H_2O$ 0.083 mmol 4,4'BPDC 0.041 mmol | DEF $H_2O_2$ $MeNH_2$ | 90 | 111.6 | 90 | 23.12 | 20.92 | 12 | C2/c |

-continued

| MOF-n | Constituents molar ratio M + L | Solvents | α | β | γ | a | b | c | Space group |
|---|---|---|---|---|---|---|---|---|---|
| MOF-69B | Zn(NO$_3$)$_2$·6H$_2$O 0.083 mmol 2,6-NCD 0.041 mmol | DEF H$_2$O$_2$ MeNH$_2$ | 90 | 95.3 | 90 | 20.17 | 18.55 | 12.16 | C2/c |
| MOF-11 Cu$_2$(ATC) | Cu(NO$_3$)$_2$·2.5H$_2$O 0.47 mmol H$_2$ATC 0.22 mmol | H$_2$O | 90 | 93.86 | 90 | 12.987 | 11.22 | 11.336 | C2/c |
| MOF-11 CU$_2$(ATC) dehydr. | | | 90 | 90 | 90 | 8.4671 | 8.4671 | 14.44 | P42/mmc |
| MOF-14 Cu$_3$ (BTB) | Cu(NO$_3$)$_2$·2.5H$_2$O 0.28 mmol H$_3$BTB 0.052 mmol | H$_2$O DMF EtOH | 90 | 90 | 90 | 26.946 | 26.946 | 26.946 | Im-3 |
| MOF-32 Cd(ATC) | Cd(NO$_3$)$_2$·4H$_2$O 0.24 mmol H$_4$ATC 0.10 mmol | H$_2$O NaOH | 90 | 90 | 90 | 13.468 | 13.468 | 13.468 | P(-4)3m |
| MOF-33 Zn$_2$ (ATB) | ZnCl$_2$ 0.15 mmol H$_4$ATB 0.02 mmol | H$_2$O DMF EtOH | 90 | 90 | 90 | 19.561 | 15.255 | 23.404 | Imma |
| MOF-34 Ni(ATC) | Ni(NO$_3$)$_2$·6H$_2$O 0.24 mmol H$_4$ATC 0.10 mmol | H$_2$O NaOH | 90 | 90 | 90 | 10.066 | 11.163 | 19.201 | P2$_1$2$_1$2$_1$ |
| MOF-36 Zn$_2$ (MTB) | Zn(NO$_3$)$_2$·4H$_2$O 0.20 mmol H$_4$MTB 0.04 mmol | H$_2$O DMF | 90 | 90 | 90 | 15.745 | 16.907 | 18.167 | Pbca |
| MOF-39 Zn$_3$O(HBTB) | Zn(NO$_3$)$_2$ 4H$_2$O 0.27 mmol H$_3$BTB 0.07 mmol | H$_2$O DMF EtOH | 90 | 90 | 90 | 17.158 | 21.591 | 25.308 | Pnma |
| NO305 | FeCl$_2$·4H$_2$O 5.03 mmol Formic acid 86.90 mmol | DMF | 90 | 90 | 120 | 8.2692 | 8.2692 | 63.566 | R-3c |
| NO306A | FeCl$_2$·4H$_2$O 5.03 mmol Formic acid 86.90 mmol | DEF | 90 | 90 | 90 | 9.9364 | 18.374 | 18.374 | Pbcn |
| NO29 MOF-0 similar | Mn(Ac)$_2$·4H$_2$O 0.46 mmol H$_3$BTC 0.69 mmol | DMF | 120 | 90 | 90 | 14.16 | 33.521 | 33.521 | P-1 |
| BPR48 A2 | Zn(NO$_3$)$_2$ 6H$_2$O 0.012 mmol H$_2$BDC 0.012 mmol | DMSO Toluene | 90 | 90 | 90 | 14.5 | 17.04 | 18.02 | Pbca |
| BPR69 B1 | Cd(NO$_3$)$_2$ 4H$_2$O 0.0212 mmol H$_2$BDC 0.0428 mmol | DMSO | 90 | 98.76 | 90 | 14.16 | 15.72 | 17.66 | Cc |
| BPR92 A2 | Co(NO$_3$)$_2$·6H$_2$O 0.018 mmol H$_2$BDC 0.018 mmol | NMP | 106.3 | 107.63 | 107.2 | 7.5308 | 10.942 | 11.025 | P1 |
| BPR95 C5 | Cd(NO$_3$)$_2$ 4H$_2$O 0.012 mmol H$_2$BDC 0.36 mmol | NMP | 90 | 112.8 | 90 | 14.460 | 11.085 | 15.829 | P2(1)/n |
| Cu C$_6$H$_4$O$_6$ | Cu(NO$_3$)$_2$·2.5H$_2$O 0.370 mmol H$_2$BDC(OH)$_2$ 0.37 mmol | DMF Chlorobenzene | 90 | 105.29 | 90 | 15.259 | 14.816 | 14.13 | P2(1)/c |
| M(BTC) MOF-0 similar | Co(SO$_4$) H$_2$O 0.055 mmol H$_3$BTC 0.037 mmol | DMF | | as MOF-0 | | | | | |
| Tb(C$_6$H$_4$O$_6$) | Tb(NO$_3$)$_3$·5H$_2$O 0.370 mmol H$_2$(C$_6$H$_4$O$_6$) 0.56 mmol | DMF Chlorobenzene | 104.6 | 107.9 | 97.147 | 10.491 | 10.981 | 12.541 | P-1 |

-continued

| MOF-n | Constituents molar ratio M + L | Solvents | α | β | γ | a | b | c | Space group |
|---|---|---|---|---|---|---|---|---|---|
| Zn (C$_2$O$_4$) | ZnCl$_2$ 0.370 mmol Oxalic acid 0.37 mmol | DMF Chlorobenzene | 90 | 120 | 90 | 9.4168 | 9.4168 | 8.464 | P(-3)1m |
| Co(CHO) | Co(NO$_3$)$_2$·5H$_2$O 0.043 mmol formic acid 1.60 mmol | DMF | 90 | 91.32 | 90 | 11.328 | 10.049 | 14.854 | P2(1)/n |
| Cd(CHO) | Cd(NO$_3$)$_2$·4H$_2$O 0.185 mmol formic acid 0.185 mmol | DMF | 90 | 120 | 90 | 8.5168 | 8.5168 | 22.674 | R-3c |
| Cu(C$_3$H$_2$O$_4$) | Cu(NO$_3$)$_2$·2.5H$_2$O 0.043 mmol Malonic acid 0.192 mmol | DMF | 90 | 90 | 90 | 8.366 | 8.366 | 11.919 | P43 |
| Zn$_6$ (NDC)$_5$ MOF-48 | Zn(NO$_3$)$_2$·6H$_2$O 0.097 mmol 14 NDC 0.069 mmol | DMF chlorobenzene H$_2$O$_2$ | 90 | 95.902 | 90 | 19.504 | 16.482 | 14.64 | C2/m |
| MOF-47 | Zn(NO$_3$)$_2$ 6H$_2$O 0.185 mmol H$_2$(BDC[CH$_3$]$_4$) 0.185 mmol | DMF chlorobenzene H$_2$O$_2$ | 90 | 92.55 | 90 | 11.303 | 16.029 | 17.535 | P2(1)/c |
| MO25 | Cu(NO$_3$)$_2$·2.5H$_2$O 0.084 mmol BPhDC 0.085 mmol | DMF | 90 | 112.0 | 90 | 23.880 | 16.834 | 18.389 | P2(1)/c |
| Cu-Thio | Cu(NO$_3$)$_2$·2.5H$_2$O 0.084 mmol thiophene Dicarboxylic acid 0.085 mmol | DEF | 90 | 113.6 | 90 | 15.4747 | 14.514 | 14.032 | P2(1)/c |
| ClBDC1 | Cu(NO$_3$)$_2$·2.5H$_2$O 0.084 mmol H$_2$(BDCCl$_2$) 0.085 mmol | DMF | 90 | 105.6 | 90 | 14.911 | 15.622 | 18.413 | C2/c |
| MOF-101 | Cu(NO$_3$)$_2$·2.5H$_2$O 0.084 mmol BrBDC 0.085 mmol | DMF | 90 | 90 | 90 | 21.607 | 20.607 | 20.073 | Fm3m |
| Zn$_3$(BTC)$_2$ | ZnCl$_2$ 0.033 mmol H$_3$BTC 0.033 mmol | DMF EtOH base added | 90 | 90 | 90 | 26.572 | 26.572 | 26.572 | Fm-3m |
| MOF-j | Co(CH$_3$CO$_2$)$_2$·4H$_2$O (1.65 mmol) H$_3$(BZC) (0.95 mmol) | H$_2$O | 90 | 112.0 | 90 | 17.482 | 12.963 | 6.559 | C2 |
| MOF-n | Zn(NO$_3$)$_2$·6H$_2$O H$_3$ (BTC) | ethanol | 90 | 90 | 120 | 16.711 | 16.711 | 14.189 | P6(3)/mcm |
| PbBDC | Pb(NO$_3$)$_2$ (0.181 mmol) H$_2$(BDC) (0.181 mmol) | DMF ethanol | 90 | 102.7 | 90 | 8.3639 | 17.991 | 9.9617 | P2(1)/n |
| Znhex | Zn(NO$_3$)$_2$·6H$_2$O (0.171 mmol) H$_3$BTB (0.114 mmol) | DMF p-xylene ethanol | 90 | 90 | 120 | 37.1165 | 37.117 | 30.019 | P3(1)c |
| AS16 | FeBr$_2$ 0.927 mmol H$_2$(BDC) 0.927 mmol | DMF anhydr. | 90 | 90.13 | 90 | 7.2595 | 8.7894 | 19.484 | P2(1)c |
| AS27-2 | FeBr$_2$ 0.927 mmol H$_3$(BDC) 0.464 mmol | DMF anhydr. | 90 | 90 | 90 | 26.735 | 26.735 | 26.735 | Fm3m |
| AS32 | FeCl$_3$ 1.23 mmol H$_2$(BDC) 1.23 mmol | DMF anhydr. ethanol | 90 | 90 | 120 | 12.535 | 12.535 | 18.479 | P6(2)c |
| AS54-3 | FeBr$_2$ 0.927 BPDC 0.927 mmol | DMF anhydr. n-Propanol | 90 | 109.98 | 90 | 12.019 | 15.286 | 14.399 | C2 |

-continued

| MOF-n | Constituents molar ratio M + L | Solvents | α | β | γ | a | b | c | Space group |
|---|---|---|---|---|---|---|---|---|---|
| AS61-4 | FeBr$_2$ 0.927 mmol m-BDC 0.927 mmol | pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. pyridine | 90 | 90 | 90 | 18.3407 | 10.036 | 18.039 | Pca2$_1$ |
| Zn(ADC) | Zn(NO$_3$)$_2$•6H$_2$O 0.37 mmol H$_2$(ADC) 0.36 mmol | DMF chloro-benzene | 90 | 99.85 | 90 | 16.764 | 9.349 | 9.635 | C2/c |
| MOF-12 Zn$_2$ (ATC) | Zn(NO$_3$)$_2$•6H$_2$O 0.30 mmol H$_4$(ATC) 0.15 mmol | ethanol | 90 | 90 | 90 | 15.745 | 16.907 | 18.167 | Pbca |
| MOF-20 ZnNDC | Zn(NO$_3$)$_2$•6H$_2$O 0.37 mmol H$_2$NDC 0.36 mmol | DMF chloro-benzene | 90 | 92.13 | 90 | 8.13 | 16.444 | 12.807 | P2(1)/c |
| MOF-37 | Zn(NO$_3$)$_2$•6H$_2$O 0.20 mmol H$_2$NDC 0.20 mmol | DEF chloro-benzene | 72.38 | 83.16 | 84.33 | 9.952 | 11.576 | 15.556 | P-1 |
| Zn(NDC) (DMSO) | Zn(NO$_3$)$_2$•6H$_2$O H$_2$NDC | DMSO | 68.08 | 75.33 | 88.31 | 8.631 | 10.207 | 13.114 | P-1 |
| Zn(NDC) | Zn(NO$_3$)$_2$•6H$_2$O H$_2$NDC | | 90 | 99.2 | 90 | 19.289 | 17.628 | 15.052 | C2/c |
| Zn(HPDC) | Zn(NO$_3$)$_2$•4H$_2$O 0.23 mmol H$_2$(HPDC) 0.05 mmol | DMF H$_2$O | 107.9 | 105.06 | 94.4 | 8.326 | 12.085 | 13.767 | P-1 |
| Co(HPDC) | Co(NO$_3$)$_2$•6H$_2$O 0.21 mmol H$_2$ (HPDC) 0.06 mmol | DMF H$_2$O/ ethanol | 90 | 97.69 | 90 | 29.677 | 9.63 | 7.981 | C2/c |
| Zn$_3$(PDC) 2.5 | Zn(NO$_3$)$_2$•4H$_2$O 0.17 mmol H$_2$(HPDC) 0.05 mmol | DMF/ ClBz H$_2$O/TEA | 79.34 | 80.8 | 85.83 | 8.564 | 14.046 | 26.428 | P-1 |
| Cd$_2$ (TPDC)2 | Cd(NO$_3$)$_2$•4H$_2$O 0.06 mmol H$_2$(HPDC) 0.06 mmol | methanol/ CHP H$_2$O | 70.59 | 72.75 | 87.14 | 10.102 | 14.412 | 14.964 | P-1 |
| Tb(PDC) 1.5 | Tb(NO$_3$)$_3$•5H$_2$O 0.21 mmol H$_2$(PDC) 0.034 mmol | DMF H$_2$O/ ethanol | 109.8 | 103.61 | 100.14 | 9.829 | 12.11 | 14.628 | P-1 |
| ZnDBP | Zn(NO$_3$)$_2$•6H$_2$O 0.05 mmol dibenzyl phosphate 0.10 mmol | MeOH | 90 | 93.67 | 90 | 9.254 | 10.762 | 27.93 | P2/n |
| Zn$_3$(BPDC) | ZnBr$_2$ 0.021 mmol 4,4'BPDC 0.005 mmol | DMF | 90 | 102.76 | 90 | 11.49 | 14.79 | 19.18 | P21/n |
| CdBDC | Cd(NO$_3$)$_2$•4H$_2$O 0.100 mmol H$_2$(BDC) 0.401 mmol | DMF Na$_2$SiO$_3$ (aq) | 90 | 95.85 | 90 | 11.2 | 11.11 | 16.71 | P21/n |
| Cd-mBDC | Cd(NO$_3$)$_2$•4H$_2$O 0.009 mmol H$_2$(mBDC) 0.018 mmol | DMF MeNH$_2$ | 90 | 101.1 | 90 | 13.69 | 18.25 | 14.91 | C2/c |
| Zn$_4$OBNDC | Zn(NO$_3$)$_2$•6H$_2$O 0.041 mmol BNDC | DEF MeNH$_2$ H$_2$O$_2$ | 90 | 90 | 90 | 22.35 | 26.05 | 59.56 | Fmmm |
| Eu(TCA) | Eu(NO$_3$)$_3$•6H$_2$O 0.14 mmol TCA 0.026 mmol | DMF chloro-benzene | 90 | 90 | 90 | 23.325 | 23.325 | 23.325 | Pm-3n |

-continued

| MOF-n | Constituents molar ratio M + L | Solvents | α | β | γ | a | b | c | Space group |
|---|---|---|---|---|---|---|---|---|---|
| Tb(TCA) | Tb(NO$_3$)$_3$•6H$_2$O 0.069 mmol TCA 0.026 mmol | DMF chlorobenzene | 90 | 90 | 90 | 23.272 | 23.272 | 23.372 | Pm-3n |
| Formates | Ce(NO$_3$)$_3$•6H$_2$O 0.138 mmol formic acid 0.43 mmol | H$_2$O ethanol | 90 | 90 | 120 | 10.668 | 10.667 | 4.107 | R-3m |
| | FeCl$_2$•4H$_2$O 5.03 mmol formic acid 86.90 mmol | DMF | 90 | 90 | 120 | 8.2692 | 8.2692 | 63.566 | R-3c |
| | FeCl$_2$•4H$_2$O 5.03 mmol formic acid 86.90 mmol | DEF | 90 | 90 | 90 | 9.9364 | 18.374 | 18.374 | Pbcn |
| | FeCl$_2$•4H$_2$O 5.03 mmol formic acid 86.90 mmol | DEF | 90 | 90 | 90 | 8.335 | 8.335 | 13.34 | P-31c |
| NO330 | FeCl$_2$•4H$_2$O 0.50 mmol formic acid 8.69 mmol | formamide | 90 | 90 | 90 | 8.7749 | 11.655 | 8.3297 | Pnna |
| NO332 | FeCl$_2$•4H$_2$O 0.50 mmol formic acid 8.69 mmol | DIP | 90 | 90 | 90 | 10.0313 | 18.808 | 18.355 | Pbcn |
| NO333 | FeCl$_2$•4H$_2$O 0.50 mmol formic acid 8.69 mmol | DBF | 90 | 90 | 90 | 45.2754 | 23.861 | 12.441 | Cmcm |
| NO335 | FeCl$_2$•4H$_2$O 0.50 mmol formic acid 8.69 mmol | CHF | 90 | 91.372 | 90 | 11.5964 | 10.187 | 14.945 | P21/n |
| NO336 | FeCl$_2$•4H$_2$O 0.50 mmol formic acid 8.69 mmol | MFA | 90 | 90 | 90 | 11.7945 | 48.843 | 8.4136 | Pbcm |
| NO13 | Mn(Ac)$_2$•4H$_2$O 0.46 mmol benzoic acid 0.92 mmol bipyridine 0.46 mmol | ethanol | 90 | 90 | 90 | 18.66 | 11.762 | 9.418 | Pbcn |
| NO29 MOF-0 similar | Mn(Ac)$_2$•4H$_2$O 0.46 mmol H$_3$BTC 0.69 mmol | DMF | 120 | 90 | 90 | 14.16 | 33.521 | 33.521 | P-1 |
| Mn(hfac)$_2$ (O$_2$CC$_6$H$_5$) | Mn(Ac)$_2$•4H$_2$O 0.46 mmol Hfac 0.92 mmol bipyridine 0.46 mmol | Ether | 90 | 95.32 | 90 | 9.572 | 17.162 | 14.041 | C2/c |
| BPR43G2 | Zn(NO$_3$)$_2$•6H$_2$O 0.0288 mmol H$_2$BDC 0.0072 mmol | DMF CH$_3$CN | 90 | 91.37 | 90 | 17.96 | 6.38 | 7.19 | C2/c |
| BPR48A2 | Zn(NO$_3$)$_2$ 6H$_2$O 0.012 mmol H$_2$BDC 0.012 mmol | DMSO toluene | 90 | 90 | 90 | 14.5 | 17.04 | 18.02 | Pbca |
| BPR49B1 | Zn(NO$_3$)$_2$ 6H$_2$O 0.024 mmol H$_2$BDC 0.048 mmol | DMSO methanol | 90 | 91.172 | 90 | 33.181 | 9.824 | 17.884 | C2/c |
| BPR56E1 | Zn(NO$_3$)$_2$ 6H$_2$O 0.012 mmol H$_2$BDC 0.024 mmol | DMSO n-Propanol | 90 | 90.096 | 90 | 14.5873 | 14.153 | 17.183 | P2(1)/n |

-continued

| MOF-n | Constituents molar ratio M + L | Solvents | α | β | γ | a | b | c | Space group |
|---|---|---|---|---|---|---|---|---|---|
| BPR68D10 | Zn(NO₃)₂ 6H₂O 0.0016 mmol H₃BTC 0.0064 mmol | DMSO benzene | 90 | 95.316 | 90 | 10.0627 | 10.17 | 16.413 | P2(1)/c |
| BPR69B1 | Cd(NO₃)₂ 4H₂O 0.0212 mmol H₂BDC 0.0428 mmol | DMSO | 90 | 98.76 | 90 | 14.16 | 15.72 | 17.66 | Cc |
| BPR73E4 | Cd(NO₃)₂ 4H₂O 0.006 mmol H₂BDC 0.003 mmol | DMSO toluene | 90 | 92.324 | 90 | 8.7231 | 7.0568 | 18.438 | P2(1)/n |
| BPR76D5 | Zn(NO₃)₂ 6H₂O 0.0009 mmol H₂BzPDC 0.0036 mmol | DMSO | 90 | 104.17 | 90 | 14.4191 | 6.2599 | 7.0611 | Pc |
| BPR80B5 | Cd(NO₃)₂·4H₂O 0.018 mmol H₂BDC 0.036 mmol | DMF | 90 | 115.11 | 90 | 28.049 | 9.184 | 17.837 | C2/c |
| BPR80H5 | Cd(NO₃)₂ 4H₂O 0.027 mmol H₂BDC 0.027 mmol | DMF | 90 | 119.06 | 90 | 11.4746 | 6.2151 | 17.268 | P2/c |
| BPR82C6 | Cd(NO₃)₂ 4H₂O 0.0068 mmol H₂BDC 0.202 mmol | DMF | 90 | 90 | 90 | 9.7721 | 21.142 | 27.77 | Fdd2 |
| BPR86C3 | Co(NO₃)₂ 6H₂O 0.0025 mmol H₂BDC 0.075 mmol | DMF | 90 | 90 | 90 | 18.3449 | 10.031 | 17.983 | Pca2(1) |
| BPR86H6 | Cd(NO₃)₂·6H₂O 0.010 mmol H₂BDC 0.010 mmol | DMF | 80.98 | 89.69 | 83.412 | 9.8752 | 10.263 | 15.362 | P-1 |
|  | Co(NO₃)₂ 6H₂O | NMP | 106.3 | 107.63 | 107.2 | 7.5308 | 10.942 | 11.025 | P1 |
| BPR95A2 | Zn(NO₃)₂ 6H₂O 0.012 mmol H₂BDC 0.012 mmol | NMP | 90 | 102.9 | 90 | 7.4502 | 13.767 | 12.713 | P2(1)/c |
| CuC₆F₄O₄ | Cu(NO₃)₂·2.5H₂O 0.370 mmol H₂BDC(OH)₂ 0.37 mmol | DMF chloro- benzene | 90 | 98.834 | 90 | 10.9675 | 24.43 | 22.553 | P2(1)/n |
| Fe Formic | FeCl₂·4H₂O 0.370 mmol formic acid 0.37 mmol | DMF | 90 | 91.543 | 90 | 11.495 | 9.963 | 14.48 | P2(1)/n |
| Mg Formic | Mg(NO₃)₂·6H₂O 0.370 mmol formic acid 0.37 mmol | DMF | 90 | 91.359 | 90 | 11.383 | 9.932 | 14.656 | P2(1)/n |
| MgC₆H₄O₆ | Mg(NO₃)₂·6H₂O 0.370 mmol H₂BDC(OH)₂ 0.37 mmol | DMF | 90 | 96.624 | 90 | 17.245 | 9.943 | 9.273 | C2/c |
| Zn C₂H₄BDC MOF-38 | ZnCl₂ 0.44 mmol CBBDC 0.261 mmol | DMF | 90 | 94.714 | 90 | 7.3386 | 16.834 | 12.52 | P2(1)/n |
| MOF-49 | ZnCl₂ 0.44 mmol m-BDC 0.261 mmol | DMF CH₃CN | 90 | 93.459 | 90 | 13.509 | 11.984 | 27.039 | P2/c |
| MOF-26 | Cu(NO₃)₂·5H₂O 0.084 mmol DCPE 0.085 mmol | DMF | 90 | 95.607 | 90 | 20.8797 | 16.017 | 26.176 | P2(1)/n |
| MOF-112 | Cu(NO₃)₂·2.5H₂O 0.084 mmol o-Br-m-BDC 0.085 mmol | DMF ethanol | 90 | 107.49 | 90 | 29.3241 | 21.297 | 18.069 | C2/c |
| MOF-109 | Cu(NO₃)₂·2.5H₂O 0.084 mmol | DMF | 90 | 111.98 | 90 | 23.8801 | 16.834 | 18.389 | P2(1)/c |

-continued

| MOF-n | Constituents molar ratio M + L | Solvents | α | β | γ | a | b | c | Space group |
|---|---|---|---|---|---|---|---|---|---|
| MOF-111 | KDB 0.085 mmol Cu(NO$_3$)$_2$•2.5H$_2$O 0.084 mmol o-BrBDC 0.085 mmol | DMF ethanol | 90 | 102.16 | 90 | 10.6767 | 18.781 | 21.052 | C2/c |
| MOF-110 | Cu(NO$_3$)$_2$•2.5H$_2$O 0.084 mmol thiophene dicarboxylic acid 0.085 mmol | DMF | 90 | 90 | 120 | 20.0652 | 20.065 | 20.747 | R-3/m |
| MOF-107 | Cu(NO$_3$)$_2$•2.5H$_2$O 0.084 mmol thiophene dicarboxylic acid 0.085 mmol | DEF | 104.8 | 97.075 | 95.206 | 11.032 | 18.067 | 18.452 | P-1 |
| MOF-108 | Cu(NO3)2•2.5H$_2$O 0.084 mmol thiophene dicarboxylic acid 0.085 mmol | DBF/ methanol | 90 | 113.63 | 90 | 15.4747 | 14.514 | 14.032 | C2/c |
| MOF-102 | Cu(NO3)2•2.5H$_2$O 0.084 mmol H2(BDCCl2) 0.085 mmol | DMF | 91.63 | 106.24 | 112.01 | 9.3845 | 10.794 | 10.831 | P-1 |
| Clbdc1 | Cu(NO3)2•2.5H$_2$O 0.084 mmol H2(BDCCl2) 0.085 mmol | DEF | 90 | 105.56 | 90 | 14.911 | 15.622 | 18.413 | P-1 |
| Cu(NMOP) | Cu(NO3)2•2.5H$_2$O 0.084 mmol NBDC 0.085 mmol | DMF | 90 | 102.37 | 90 | 14.9238 | 18.727 | 15.529 | P2(1)/m |
| Tb(BTC) | Tb(NO3)3•5H$_2$O 0.033 mmol H3BTC 0.033 mmol | DMF | 90 | 106.02 | 90 | 18.6986 | 11.368 | 19.721 | |
| Zn3(BTC)2 Honk | ZnCl2 0.033 mmol H3BTC 0.033 mmol | DMF ethanol | 90 | 90 | 90 | 26.572 | 26.572 | 26.572 | Fm-3m |
| Zn4O(NDC) | Zn(NO3)2•4H$_2$O 0.066 mmol 14NDC 0.066 mmol | DMF ethanol | 90 | 90 | 90 | 41.5594 | 18.818 | 17.574 | aba2 |
| IRMOF-2 | Zn(NO3)2•4H$_2$O 0.160 mmol o-Br-BDC 0.60 mmol | DEF | 90 | 90 | 90 | 25.772 | 25.772 | 25.772 | Fm-3m |
| IRMOF-3 | Zn(NO3)2•4H$_2$O 0.20 mmol H2N-BDC 0.60 mmol | DEF ethanol | 90 | 90 | 90 | 25.747 | 25.747 | 25.747 | Fm-3m |
| IRMOF-4 | Zn(NO3)2•4H$_2$O 0.11 mmol [C3H7O]2-BDC 0.48 mmol | DEF | 90 | 90 | 90 | 25.849 | 25.849 | 25.849 | Fm-3m |
| IRMOF-5 | Zn(NO3)2•4H$_2$O 0.13 mmol [C5H11O]2-BDC 0.50 mmol | DEF | 90 | 90 | 90 | 12.882 | 12.882 | 12.882 | Pm-3m |
| IRMOF-6 | Zn(NO3)2•4H$_2$O 0.20 mmol [C2H4]-BDC 0.60 mmol | DEF | 90 | 90 | 90 | 25.842 | 25.842 | 25.842 | Fm-3m |
| IRMOF-7 | Zn(NO3)2•4H$_2$O 0.07 mmol 1,4NDC 0.20 mmol | DEF | 90 | 90 | 90 | 12.914 | 12.914 | 12.914 | Pm-3m |
| IRMOF-8 | Zn(NO3)2•4H$_2$O 0.55 mmol 2,6NDC 0.42 mmol | DEF | 90 | 90 | 90 | 30.092 | 30.092 | 30.092 | Fm-3m |
| IRMOF-9 | Zn(NO3)2•4H$_2$O 0.05 mmol | DEF | 90 | 90 | 90 | 17.147 | 23.322 | 25.255 | Pnnm |

| MOF-n | Constituents molar ratio M + L | Solvents | α | β | γ | a | b | c | Space group |
|---|---|---|---|---|---|---|---|---|---|
| IRMOF-10 | BPDC 0.42 mmol Zn(NO3)2·4H₂O 0.02 mmol | DEF | 90 | 90 | 90 | 34.281 | 34.281 | 34.281 | Fm-3m |
| IRMOF-11 | BPDC 0.012 mmol Zn(NO3)2·4H₂O 0.05 mmol | DEF | 90 | 90 | 90 | 24.822 | 24.822 | 56.734 | R-3m |
| IRMOF-12 | HPDC 0.20 mmol Zn(NO3)2·4H₂O 0.017 mmol | DEF | 90 | 90 | 90 | 34.281 | 34.281 | 34.281 | Fm-3m |
| IRMOF-13 | HPDC 0.12 mmol Zn(NO₃)₂·4H₂O 0.048 mmol | DEF | 90 | 90 | 90 | 24.822 | 24.822 | 56.734 | R-3m |
| IRMOF-14 | PDC 0.31 mmol Zn(NO₃)₂·4H₂O 0.17 mmol | DEF | 90 | 90 | 90 | 34.381 | 34.381 | 34.381 | Fm-3m |
| IRMOF-15 | PDC 0.12 mmol Zn(NO₃)₂·4H₂O 0.063 mmol | DEF | 90 | 90 | 90 | 21.459 | 21.459 | 21.459 | Im-3m |
| IRMOF-16 | TPDC 0.025 mmol Zn(NO₃)₂·4H₂O 0.0126 mmol TPDC 0.05 mmol | DEF NMP | 90 | 90 | 90 | 21.49 | 21.49 | 21.49 | Pm-3m |

ADC Acetylenedicarboxylic acid
NDC Naphthalenedicarboxylic acid
BDC Benzenedicarboxylic acid
ATC Adamantanetetracarboxylic acid
BTC Benzenetricarboxylic acid
BTB Benzenetribenzoic acid
MTB Methanetetrabenzoic acid
ATB Adamantanetetrabenzoic acid
ADB Adamantanedibenzoic acid Further metal-organic frameworks are MOF-2 to 4, MOF-9, MOF-31 to 36, MOF-39, MOF-69 to 80, MOF103 to 106, MOF-122, MOF-125, MOF-150, MOF-177, MOF-178, MOF-235, MOF-236, MOF-500, MOF-501, MOF-502, MOF-505, IRMOF-1, IRMOF-61, IRMOP-13, IRMOP-51, MIL-17, MIL-45, MIL-47, MIL-53, MIL-59, MIL-60, MIL-61, MIL-63, MIL-68, MIL-79, MIL-80, MIL-83, MIL-85, CPL-1 to 2, SZL-1, which are described in the literature.

Particularly preferred metal-organic frameworks are MIL-53, Zn-tBu-sophthalic acid, Al-BDC, MOF-5, MOF-177, MOF-505, IRMOF-8, IRMOF-11, Cu-BTC, Al-NDC, Al-aminoBDC, Cu-BDC-TEDA, Zn-BDC-TEDA, Al-BTC, Cu-BTC, Al-NDC, Mg-NDC, Al-fumarate, Zn-2-aminoimidazolate, Cu-biphenyldicarboxylate-TEDA, MOF-74, Cu-BPP, Sc-terephthalate. Greater preference is given to Sc-terephthalate, Al-BDC and Al-BTC.

Even more preferred metal-organic framework materials are Zn-BTB, Mg-2,6-dihydroxyterephthalate, Al-fumarate and Cu-1,3,5-BTC, especially Zn-BTB, Al-fumarate, Cu-1,3,5-BTC.

Apart from the conventional method of preparing the MOFs, as described, for example, in U.S. Pat. No. 5,648,508, they can also be prepared by an electrochemical route. In this regard, reference is made to DE-A 103 55 087 and WO-A 2005/049892. The metal-organic frameworks prepared in this way have particularly good properties in respect of the adsorption and desorption of chemical substances, in particular gases.

Regardless of the method of preparation, the metal-organic framework is obtained in pulverulent or crystalline form. It is preferably used as loose material. The metal-organic framework can also be converted into a shaped body.

Accordingly, in a preferred embodiment, the metal-organic framework material is used in step (a) in form of shaped bodies. Preferably, before step (a) the shaped bodies are crushed.

Preferred processes for shaping are extrusion or tableting. In the production of shaped bodies, further materials such as binders, lubricants or other additives can be added to the metal-organic framework. It is likewise conceivable to produce mixtures of framework and other adsorbents such as activated carbon as shaped bodies or for them to form separate shaped bodies which are then used as mixtures of shaped bodies.

According to the present invention these further materials, like graphite, can be easily separated by means known in the art, like filtration, when the organic compound and optionally the metal ion are in solved form.

The possible geometries of these shaped bodies are in principle not subject to any restrictions. For example, possible shapes are, inter alia, pellets such as disk-shaped pellets, pills, spheres, granules, extrudates such as rods, honeycombs, grids or hollow bodies.

The metal-organic framework is preferably present as crushed shaped bodies. Preferred embodiments are tablets and elongated extrudates. Methods for crushing are known in the ar. Crushing can be obtained, e.g., via malt milling, bell milling, applying mechanical force by wheeling, sonification or the like.

The shaped bodies—before crushing—preferably have a dimension in one direction in space in the range from 0.2 mm to 30 mm, more preferably from 0.5 mm to 5 mm, in particular from 1 mm to 3 mm.

To produce the shaped bodies, it is in principle possible to employ all suitable methods. In particular, the following processes are preferred:

Kneading of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

Application of the framework to at least one optionally porous support material. The material obtained can then be processed further by the above-described method to give a shaped body.

Application of the framework to at least one optionally porous substrate.

Kneading and shaping can be carried out by any suitable method, for example as described in Ulmanns Enzyklopädie der Technischen Chemie, 4th edition, volume 2, p. 313 ff. (1972), whose relevant contents are fully incorporated by reference into the present patent application.

For example, the kneading and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the desired viscosity for the kneading and/or shaping of the composition to be kneaded and/or shaped. Accordingly, binders can, for the purposes of the present invention, be either viscosity-increasing or viscosity-reducing compounds.

Preferred binders are, for example, Inter alia aluminum oxide or binders comprising aluminum oxide, as are described, for example, in WO 94/29408, silicon dioxide as described, for example, in EP 0 592 050 A1, mixtures of silicon dioxide and aluminum oxide, as are described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, or, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols, amphiphilic substances and/or graphites. Particular preference is given to graphite.

As viscosity-increasing compound, it is, for example, also possible to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of the additives such as template compound, binder, pasting agent, viscosity-increasing substance during shaping and kneading is in principle not critical.

In a further, preferred embodiment, the shaped body obtained by kneading and/or shaping is subjected to at least one drying step which is generally carried out at a temperature in the range from 25 to 300° C., preferably in the range from 50 to 300° C. and particularly preferably in the range from 100 to 300° C. It is likewise possible to carry out drying under reduced pressure or under a protective gas atmosphere or by spray drying.

In a particularly preferred embodiment, at least one of the compounds added as additives is at least partly removed from the shaped body during this drying process.

Accordingly, in case of shaped bodies (irrespective whether or not crushed) are used it is possible that also additives from the shaping process are comprised. When using an alkaline liquid in step (a) these additives can be separated off in step (b) when they are not solvable. Thus, alkaline solution is preferred in step (a). In case the additives are soluble in acids then the acidic solution is preferred.

However according to the present invention the total amount of additives in a shaped body (crushed or uncrushed) should be low and preferably at most 25 weight-% (even more preferably 10%, even more preferably 5%, even more preferably 3%) based on the total weight of the shaped body. Also the number of different additives should be low, preferably only 5 or less (preferably only 3 or less, even more preferably only 2 or less). As a particular additive, graphite should be mentioned.

In step (a) the metal-organic framework material is treated with an acidic or alkaline liquid. Preferably, the liquid is an aqueous liquid. According to the invention the term "aqueous" encompasses water and mixtures of water with miscible liquids, like alcohols, for example ethanol, methanol or the like. The mixture contains preferably at least 50% (V/V), more preferably 75%, more preferably 90% and even more preferably is the liquid water.

The liquid used in step (a) can be an acidic liquid. In such a case the preferred pH of said liquid is a pH of less than 4, more preferably, less than 3, even more preferably less than 2, even more preferably the pH is 1 or lower. When the liquid is an acidic liquid then the at least bidentate organic compound is preferably isolated from the solid residue obtained in step (b).

The pH can be adjusted by adding common inorganic acids, like hydrochloric acid, sulfuric acid, nitric acid.

In step (a) the liquid can be an alkaline liquid, which is preferred. Then the alkaline liquid preferably has a pH of more than 10, more preferably more than 11, even more than 12 and even more than 13. The pH can be adjusted by adding common inorganic bases, like sodium hydroxide, potassium hydroxide, ammonia.

It is preferred that an alkaline liquid is used.

The at least bidentate organic compound can be isolated in step (c) from the liquid, optionally after acidification. Methods for separating off the at least bidentate organic compound after acidification are known in the art.

It is possible that the at least one metal ion is also recovered. Methods for the isolation of the metal ion are known in the art. If an alkaline solution is used, the optional step (b) is mandatory so that the metal ion is comprised or consists of the solid residue. Further purification steps can follow. If an acidic solution is used step (c) results in the isolation of the organic compound and a solution containing the metal ion. The following isolation of the metal ion can then be carried out by methods known in the art, like precipitation reactions, Ion exchange, or the like.

Preferably, in step (a) the metal-organic framework material is treated with the acidic or alkaline liquid by contacting the material with the liquid and mixing, like be means of agitating.

Preferably, step (a) is carried out at room temperature. It is clear to the practitioner in the art that also higher temperatures can be used.

EXAMPLES

Example 1

Basolite Z377 (MOF-177, Zn-BTB)

1.1. Synthesis Basolite Z377 According to Following Example:

Under a nitrogen atmosphere 216 g $Zn(NO_3)_2 \cdot 6 H_2O$ was dissolved in 6 l dietylformamide (DEF). Under stirring 60 g 1,3,5-Tri-(4-carboxyphenyl)-benzene (BTB) was added. The resulting solution was heated up to 100° C. without stirring and kept at this temperature for 24 h. After cooling down to room temperature the obtained crystals were separated from the mother liquor, washed 4 times with 0.90 l Diethylformamide (60° C.) and 10 times with 0.9 l chloroform (50° C.). The obtained yellow crystals were dried for 3 h at room temperature at 20 mbar. Further activation was performed at full vacuum rising the temperature slowly to 130° C. until no loss on drying was observable anymore. 58.9 g of Zn-MOF could be isolated (75% yield on BTB). The Langmuir surface area was found to be 4627 m²/g.

1.2. Recycling Procedure Employing NaOH and HCl:

In a beaker containing 500 ml of distilled water 20.0 g caustic soda (NaOH, 500 mmol) was dissolved. Under stirring 57.4 g Basolite Z377 (Zn-BTB-MOF, 50 mmol) of example 1.1 was added (pH 13.21). After stirring for 1 h at room temperature not dissolved solid material was separated by filtration. The filter cake was washed three times with 50 ml distilled water. The obtained filter cake (No-1) was dried at 120° C. for 16 h giving 14.5 g of a white solid. The carbon content by elemental analysis was 1.2 g/100 g. The recovered yield on Zinc was 72%.

The pH of the combined filtrate was brought to acidic conditions (pH=1) by adding 65.16 g hydrochloric acid (32%, 571 mmol) and stirred for 30 min to precipitate the BTB linker. The precipitate was isolated via filtration, and washed with in total 2 l of distilled water. The obtained filter cake (No-2) was dried at 120° C. for 16 h giving 39.1 g of a yellow solid. The elemental analysis revealed only traces of impurities: Zn 0.005%; Na 0.033%; Cl 0.05%. The carbon content was found to be 70.5 g/100 g. The recovered yield on BTB was 89%. NMR analysis revealed high purity. The BTB material could be used in a procedure for new MOF-177 preparation as given in example 1.1 with comparable characteristics.

$^1$H-NMR (DMSO-$d_6$, 500.13 MHz): δ=13.04 (s, 3 H), 8.08 (m, 12 H).

$^{13}$C-NMR (DMSO-$d_6$, 125.77 MHz): δ=167.18, 143.79, 140.68, 129.92, 129.91, 127.53, 127.34, 125.50.

1.3. Synthesis of Basolite Z377 Employing BTB from Example 1.2

Under a nitrogen atmosphere 64.8 g $Zn(NO_3)_2 \cdot 6 H_2O$ (Sigma-Aldrich, 22,873-7) was dissolved in 1800 ml DEF. Under stirring 18.0 g 1,3,5-Tri-(4-carboxyphenyl)-benzene (BTB) from example 1.2 was added (pH 3.94). The resulting solution was heated up to 100° C. without stirring and kept at this temperature for 24 h. After cooling down to room temperature the obtained crystals were separated from the mother liquor, washed 4 times with 0.25 l Diethylformamide and extracted with hot chloroform for 16 h in a Soxhlett extractor. The obtained yellow crystals were dried for 3 h at room temperature at 20 mbar. Further activation was performed at full vacuum rising the temperature slowly to 130° C. until no loss on drying was observable anymore. 20.94 g of Zn-MOF could be isolated (88.9% yield on BTB) with a tamped density of 220 g/l. The Langmuir surface area was found to be 4509 m²/g and the hydrogen uptake at 77 K at 1 bar to be 142.2 ccm/g.

1.4. Recycling Procedure Employing HCl:

In a beaker 11.48 g Basolite Z377 (10 mmol) from example 1.1 is suspended in 100 ml of distilled water (pH 6.77) at room temperature. Under stirring pH is adjusted to pH=1 and kept at this pH for 1 h via addition of 32% hydrochloric acid (in total 8.95 g). The precipitate is filtered of and washed with 1 liter of distilled water. The obtained filter cake was dried at 120° C. for 16 h giving 8.0 g of a white solid. The carbon content by elemental analysis was 71.6 g/100 g, the zinc content was 0.61 g/100 g. The recovered yield on BTB was 91.3%.

Example 2

Basolite A520 (Aluminum Fumarate MOF) Tablets 2.1. Synthesis Basolite A520 According to Following Example:

The material that was applied was prepared as described in WO-A 2012/042410. Its surface area ranged from 1200-1300 m²/g. Shaped bodies were prepared by thoroughly mixing the obtained Basolite A520 powder with 1.5 wt % of graphite for 0.05 h and subsequently shaping it to 3×3 mm tablets on a Korsch SP300 tableting press (filling height powder: 7.8 mm). The Langmuir surface area of the tablets was 1157 m$^2$/g, the lateral crush strength 19.2 N.

2.2. Recycling Procedure Employing NaOH and HCl:

In a beaker containing 150 ml of distilled water 12.0 g caustic soda (NaOH, 300 mmol) was dissolved. Under stirring 14.22 g crushed tablets of Basolite A520 (Al-Fumarate-MOF, 90 mmol) were added (pH 13.33). After stirring for 1 h at room temperature not dissolved solid material was separated by filtration. The filter cake was washed three times with 20 ml distilled water. The obtained filter cake (No-1) was dried at 120° C. for 16 h giving 0.01 g of a black solid (graphite additive of the tablets).

The pH of the combined filtrate was brought to acidic conditions (pH=1) by adding 63.4 g hydrochloric acid (32%, 556 mmol) and stirred for 30 min to precipitate the fumaric acid linker. The precipitate was isolated via filtration and then washed four times with each 25 ml of distilled water. The obtained filter cake (No-2) was dried at 120° C. for 16 h giving 7.36 g of a white solid. The carbon content by elemental analysis was found to be 40.4 g/100 g, the aluminum content to be 0.9 g/100 g.

An $^1$H and $^{13}$C-NMR analysis revealed a high purity of the obtained fumaric acid linker. The recovered yield was 70.4%.

$^1$H-NMR (DMSO-d$_6$, 500.13 MHz): δ=12.99 (s, 2 H), 6.65 (s, 2 H).

$^{13}$C-NMR (DMSO-d$_6$, 125.77 MHz): δ=166.3, 134.3, 133.7.

Example 3

Basolite C300 (HKUST-1)

3.1. Synthesis Basolite C300 According to Following Example:

The material was synthesized according to WO-A 2007/090809. Its surface area ranged from 1900-2100 m$^2$/g. Shaped bodies were prepared by thoroughly mixing the obtained Basolite C300 powder with 1.0 wt % of graphite for 0.05 h and subsequently shaping it to 3×3 mm tablets on a Horn tableting press. The Langmuir surface area of the tablets was 1409 m$^2$/g, the lateral crush strength 15 N.

3.2. Recycling Procedure Employing NaOH and HCl:

In a beaker containing 200 ml of distilled water 8.0 g caustic soda (NaOH, 200 mmol) was dissolved. Under stirring 12.1 g crushed tablets of Basolite C300 (Cu-BTC, 20 mmol) were added (pH 13.54). After stirring for 1 h at room temperature not dissolved solid material was separated by filtration. The filter cake was washed three times with 20 ml distilled water. The obtained filter cake (No-1) was dried at 120° C. for 16 h giving 4.32 g of a black solid (Mixture of copper hydroxide and graphite additive of the tablets). The carbon content by elemental analysis was 8.4 g/100 g.

The pH of the combined filtrate was brought to acidic conditions (pH=1) by adding 24.36 g hydrochloric acid (32%, 214 mmol) and stirred for 30 min to precipitate the BTC linker. The precipitate was isolated via filtration and then washed in total with 600 ml of distilled water. The obtained filter cake (No-2) was dried at 120° C. for 16 h giving 4.76 g of a white solid. The carbon content by elemental analysis was found to be 51.4 g/100 g, the copper content to be less than 0.001 g/100 g.

An $^1$H and $^{13}$C-NMR analysis revealed a high purity of the obtained BTC linker. The recovered yield on BTC was 56.7%.

$^1$H-NMR (DMSO-d$_6$, 500.13 MHz): δ=13.00 (s, 3 H), 8.65 (s, 3 H).

$^{13}$C-NMR (DMSO-d$_6$, 125.77 MHz): δ=165.9, 133.6, 131.8.

The invention claimed is:

1. Process for the recovery of a bidentate organic compound from a porous metal-organic framework material, the metal-organic framework material comprising the bidentate organic compound coordinated to at least one metal ion, the process comprising:
   (a) treating a metal-organic framework material with an acidic or alkaline liquid;
   (b) optionally separating solid residue; and
   (c) isolating the bidentate organic compound.

2. The process of claim 1, wherein in step (a) the acidic or alkaline liquid is an aqueous liquid.

3. The process of claim 1, wherein in step (a) the liquid is an acidic liquid.

4. The process of claim 3, wherein the acidic liquid has a pH of less than 4.

5. The process of claim 3, comprising the separation of the solid residue of step (b), and the bidentate organic compound is isolated from the solid residue.

6. The process of claim 1, wherein in step (a) the liquid is an alkaline liquid.

7. The process of claim 6, wherein the alkaline liquid has a pH of more than 10.

8. The process of claim 1, wherein the bidentate organic compound is isolated in step (c) from the acidic or alkaline liquid.

9. The process of claim 3, wherein the bidentate organic compound is isolated in step (c) from the acidic liquid.

10. The process of claim 1, further comprising recovering the at least one metal ion.

11. The process of claim 1, wherein the metal-organic framework material to be treated in step (a) is in a form of crushed shaped bodies.

12. The process of claim 1, wherein the bidentate organic compound is derived from a di- tri- or tetracarboxylic acid.

13. The process of claim 1, wherein the bidentate organic compound is derived from an organic compound selected from the group consisting of 1,3,5-tri-(4-carboxyphenyl)-benzene, benzenetricarboxylic acid, dihydroxyterephthalic acid, and fumaric acid.

14. The process of claim 1, wherein the at least one metal ion is selected from the group metals consisting of Mg, Al, Li, Ca, Zr, Ti, V, Cr, Mo, Fe, Co, Cu, Ni, Zn, and La.

15. The process of claim 1, wherein the bidentate organic compound is derived from an organic compound selected from the group consisting of phthalic acid, isophthalic acid, terephthalic acid, 2,6-naphthalenedicarboxylic acid, 1,4-naphthalenedicarboxylic acid, 1,5-naphthalene-dicarboxylic acid, 1,2,3-benzenetricarboxylic acid, 1,2,4-benzenetricarboxylic acid, 1,3,5-benzenetricarboxylic acid, 1,2,4,5-benzenetetracarboxylic acid, aminoterephthalic acid, fumaric acid, biphenyldicarboxylate, 1,5- and 2,6-naphthalenedicarboxylic acid, tert-butylisophthalic acid, dihydroxybenzoic acid, benzenetribenzoate , tetrahydropyrene-2,7-dicarboxylic acid, 1,3,5-tri-(4-carboxyphenyl)-benzene, benzenetricarboxylic acid, dihydroxyterephthalic acid, and biphenyltetracarboxylic acid.

16. The process of claim 15, wherein the at least one metal ion is selected from the group metals consisting of Mg, Al, Cu, and Zn.

17. The process of claim 1, wherein the treating of the metal-organic framework material comprises contacting the material with the liquid and mixing.

18. The process of claim 1, wherein the treating of the metal-organic framework material is carried out at room temperature.

* * * * *